United States Patent [19]

Rahm et al.

[11] 4,310,488

[45] Jan. 12, 1982

[54] SAMPLE OR REAGENT CONTAINER FOR ANALYZERS

[75] Inventors: Jürg Rahm, Basel; Lothar Waltz, Ettingen, both of Switzerland

[73] Assignee: Hoffmann-La Roche Inc., Nutley, N.J.

[21] Appl. No.: 151,240

[22] Filed: May 19, 1980

[51] Int. Cl.³ .......................... B01L 3/00; B65D 23/12
[52] U.S. Cl. ................................ 422/102; 215/100 R; 220/23.4; 220/85 H
[58] Field of Search .......................... 435/291, 32, 33; 128/295, 760; 220/70, 69, 1 R, 85 H, 23.4, 23.6; 215/100 R, 1 C; 422/99, 102; 356/246

[56] References Cited

U.S. PATENT DOCUMENTS

| | | | |
|---|---|---|---|
| 2,116,489 | 5/1903 | Jackson | 220/23.6 |
| 3,190,731 | 6/1965 | Weiskopf | 422/102 |
| 3,540,856 | 11/1970 | Rochte et al. | 422/101 |
| 4,070,249 | 1/1978 | Janin et al. | 435/300 |

Primary Examiner—William F. Smith
Assistant Examiner—Chris Konkol
Attorney, Agent, or Firm—Jon S. Saxe; Bernard S. Leon; James H. Callwood

[57] ABSTRACT

A tubular sample or reagent container for analytical devices, such as automated centrifugal analyzers, in which typically a multiplicity of such containers are arranged in a carrier plate or other means which forms part of the analyzers, with each container having a peripheral edge for bearing on the carrier plate. An abutment is provided on the containers disposed below the peripheral edge and at the periphery of the containers, which abutment is deformable in the centripetal direction.

4 Claims, 3 Drawing Figures

SAMPLE OR REAGENT CONTAINER FOR ANALYZERS

BACKGROUND OF THE INVENTION

The invention relates to a plastics tubular sample and reagent container for analyzers comprising an automatic pipetting means, said container having a peripheral edge for bearing on a plate forming part of the analyzer and serving as carrier of the containers.

Recently, particularly in clinical analysis, frequent use has been made of automatic analyzers, e.g. those operating on the centrifugal principle and making photometric measurements of the sample for analysis. The devices can be used, for example, for determining glucose, urea, uric acid, cholestrol or total protein, albumin, bilirubin or metal ions in the blood, serum, plasma, urine or fluid obtained by puncture, e.g. liquor or similar biological solutions. The amount of material available for investigation is often a few microliters, and the time available for analysis is often limited to a few minutes. In such cases it is advantageous to use automatic analyzers, which often are associated with an automatic pipetting means. The samples for analysis, as well as the reagent liquids and inert solutions, if necessary, are poured into tubular containers before the device is started up. After the containers have been filled they are inserted in apertures in a plate. The apertures are usually formed in a circle in the plate, and the filled containers are simply inserted in the individual apertures. Nearly the entire length of the containers extends through the apertures, but the container has a widened peripheral edge which bears on the plate. After the device has been started up, the pipetting means takes a preprogrammed amount from the sample and reagent containers and supplies it to the actual analyzer.

A device of the aforementioned kind is described, for example, in a pamphlet published in 1978 by Messrs. F. Hoffmann-La Roche & Co., of Basle, Switzerland, concerning the commercially available "Cobas-Bio" analyzer.

Great care, of course, must be taken when filling the sample holders with material for investigation and the reagent holders with the required reagents. Since a single plate can hold up to say twenty-five sample or reagent containers and it is not necessary to fill all the containers during every operation of the analyzer, it is desirable to have a simple method of marking those containers which are filled with material for analysis or reagents, or those containers which are not to be included in the analysis in progress. In the known systems, the usual method is to put a spot of paint on the edge or cover of the container.

SUMMARY OF THE INVENTION

An object of the invention is to simplify the marking of the containers and, more particularly, make it independent of other aids.

To this end, the invention provides an additional abutment disposed below the edge of the periphery of the container and deformable in the centripetal direction.

The object achieved by the additional abutment is that, when the container is gently inserted in the appropriate aperture of the plate, it first enters the aperture only as far as the additional abutment. It is only after slight pressure has been exerted by the finger on the surface of the container that the additional abutment is deformed in the centripetal direction, and the container slips further into the aperture until its normally-provided edge finally bears on the plate. When the device is in operation, it can easily be arranged that all filled containers are pressed deeply into the plate apertures, whereas unfilled or not-yet filled containers or those not needed for the analysis in progress are pressed only as far as the additional abutment, It will thus be visible at a glance which containers are already full and which are ready to receive additional material or are not included in the current analysis.

The proposed additional abutment can be in the form of a bead extending completely or partly around the container's periphery. Alternatively, it can comprise one or more projections formed, for example, on the outer periphery of the container and projecting radially. It is important that the additional abutment be easily deformable so that it can yield to simple pressure from the finger, and the container can be pressed to the maximum depth into the aperture in the plate. It has been found advantageous to have the additional abutment disposed in the upper part of the container.

BRIEF DESCRIPTION OF THE DRAWING

The invention will now be explained in detail with reference to the accompanying drawing, in which.

DESCRIPTION OF THE PREFERRED EMBODIMENT

Figure 1:
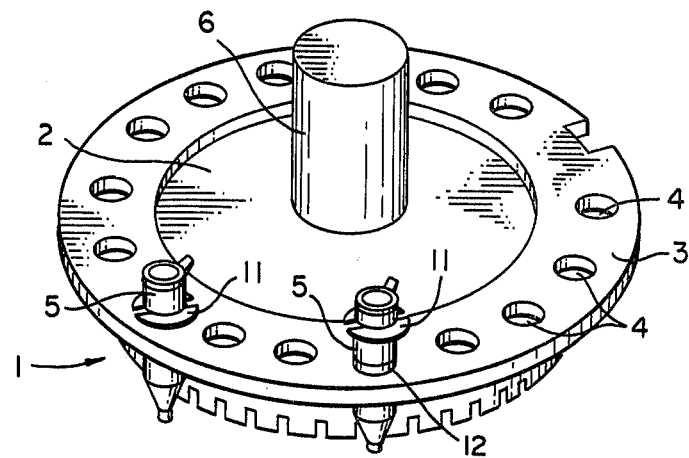
FIG. 1 is a perspective view of a plate in which two containers according to the invention are inserted.

FIG. 1 shows a plate (general reference 1). The plate comprises a plastics body 2 integral with an edge 3 formed with a number of apertures 4 for receiving containers 5. At the center of the plate there is a cylinder 6 for inserting the plate in the pipetting means of the analyzer.

Figure 2:
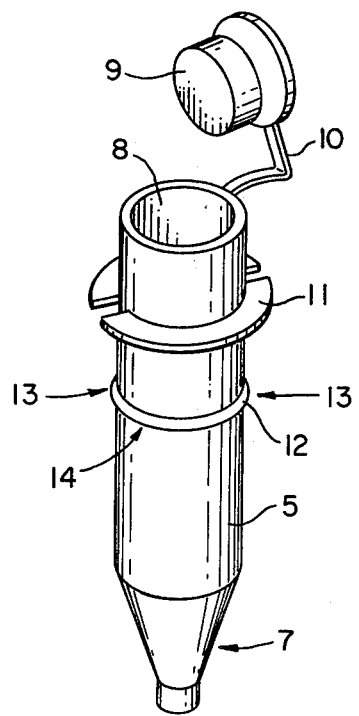
FIG. 2 shows an embodiment of a container according to the invention, in which the additional abutment is a bead.
Figure 3:
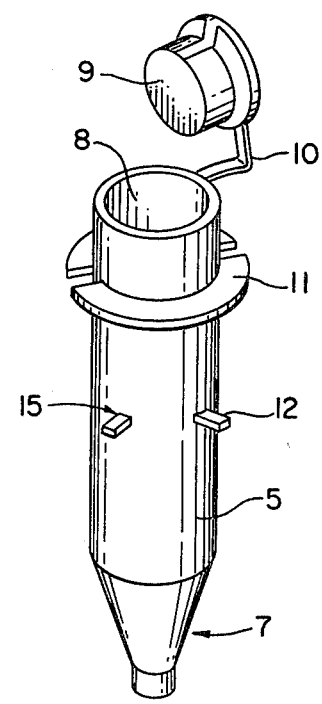
FIG. 3 shows another embodiment of the container according to the invention, in which the additional abutment comprises projections.

FIG. 1 and, more particularly, FIGS. 2 and 3 show that the sample or reagent container 5 substantially comprises a tubular main body, which has a conical point and is closed at its bottom 7. At the opposite end there is a filling opening 8 which, in the illustrated example, can be closed by a cap or cover 9. Cover 9 is nonreleasably secured to the top end of container 5 by a plastics flap 10.

After the container has been filled, cover 9 is inserted in the filling opening 8, whereupon the container is inserted into an aperture 4 in plate 1. After the analyzer has been started up, a sampling needle from the automatic pipetting means penetrates the cover and removes the preprogrammed amount from the container.

As also shown in the drawing, container 5 has a peripheral edge 11 which bears on the plate and prevents the container falling any further through aperture 4. According to the invention, the containers have an additional abutment 12 formed on the outer periphery below edge 11. The additional abutment is deformable in the centripetal direction. It can thus hold the container initially in the position shown at the lower right side of the plate of FIG. 1, but after slight pressure has been exerted on the top, the container can pass through aperture 4 and be brought into the position shown at the lower left side of the plate of FIG. 1.

The additional abutment can have various forms. FIG. 2 shows the case where abutment 12 is in the form of a bead 14 extending completely around the periphery. FIG. 3 shows another embodiment, in which the abutment 12 comprises a number of projections 15. Of course, the abutment can also be deformed if, when pressure is exerted on the top of the container, the flexible container wall yields so that the abutment can pass through aperture 4.

Preferably, the additional abutment 12 is disposed at the upper part of container 5 as shown in the drawings. Containers 5 are preferably made of high density polyethylene (HD PE). The diameter of abutment 12 is, for example, between 8.30 and 8.35 mm, in which case apertures 4 will preferably have a diameter between 8.20 and 8.24 mm.

We claim:
1. A tubular sample or reagent container for analytical devices, in particular centrifugal analyzers, the body of the container being insertable in apertures in a plate forming part of the analyzer and serving as carrier of the container, which has at its upper part a peripheral edge for bearing on said plate the improvement comprising an abutment disposed below the peripheral edge of the container and deformable in the centripetal direction.
2. A container according to claim 1 wherein the abutment is in the form of a bead extending at least partly around the periphery of the container.
3. A container according to claim 1 wherein the abutment comprises at least one projection.
4. A container according to any one of the preceding claims wherein the abutment is disposed at the upper part of the container.

* * * * *